(12) United States Patent
den Braber

(10) Patent No.: US 9,332,775 B2
(45) Date of Patent: May 10, 2016

(54) SPINACH HYBRID 51-326

(75) Inventor: Jan Hugo den Braber, Klundert (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 232 days.

(21) Appl. No.: 13/595,274

(22) Filed: Aug. 27, 2012

(65) Prior Publication Data

US 2013/0055455 A1 Feb. 28, 2013

Related U.S. Application Data

(60) Provisional application No. 61/528,944, filed on Aug. 30, 2011.

(51) Int. Cl.
| | | |
|---|---|---|
| *A01H 1/00* | (2006.01) |
| *C07H 21/04* | (2006.01) |
| *C07K 14/415* | (2006.01) |
| *C12N 15/00* | (2006.01) |
| *A23L 1/212* | (2006.01) |
| *A01H 5/12* | (2006.01) |
| *C12Q 1/68* | (2006.01) |

(52) U.S. Cl.
CPC ............. *A23L 1/2123* (2013.01); *A01H 5/12* (2013.01); *C12Q 1/6895* (2013.01); *C12Q 2600/156* (2013.01)

(58) Field of Classification Search
CPC ...... A23L 1/2123; A01H 5/12; C12Q 1/6895; C12Q 2600/156
USPC ........................................................ 800/295
See application file for complete search history.

(56) References Cited

U.S. PATENT DOCUMENTS

| | | | | |
|---|---|---|---|---|
| 7,935,867 B2* | 5/2011 | Baerends | ....................... | 800/295 |
| 2009/0300785 A1* | 12/2009 | Baerends | ....................... | 800/268 |
| 2012/0222147 A1* | 8/2012 | Dijkstra | ....................... | 800/260 |

* cited by examiner

*Primary Examiner* — Li Zheng
(74) *Attorney, Agent, or Firm* — Vedder Price P.C.; Thomas J. Kowalski; Deborah L. Lu

(57) ABSTRACT

The present invention relates to the development of a spinach plant that expresses a new resistance pattern against downy mildew (*Peronospora farinosa* f. sp. *spinaciae*) strains Pf1-Pf13, methods and compositions relating to plants, progeny, seeds and derivatives thereof and plants, progeny, seeds and derivatives thereof having all the morphological, physiological and/or genetic characteristics thereof.

14 Claims, 1 Drawing Sheet

Shape First Foliage Leaves
___ Shape:   1 = Elliptic   2 = Circular   3 = Ovate
        
___ Base:    1 = V-shape    2 = Straight   3 = Lobed
    
___ Tip:     1 = Round      2 = Round-pointed   3 = Pointed

SPINACH HYBRID 51-326

RELATED APPLICATIONS AND INCORPORATION BY REFERENCE

This application claims priority to U.S. provisional patent application Ser. No. 61/528,944 filed Aug. 30, 2011.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to the development of a spinach plant that expresses a new resistance pattern against downy mildew (*Peronospora farinosa* f. sp. *spinaciae*) strains Pf1-Pf13.

BACKGROUND OF THE INVENTION

Spinach (*Spinacia oleracea*) is a flowering vegetable plant in the family of the Amaranthaceae. It is native to southwestern and central Asia, but nowadays is being cultivated worldwide, mostly in temperate regions. The consumable parts of spinach are the leaves. These are produced during the first stage of the life cycle of a spinach plant, during which the plant forms a leaf rosette. The second stage is the flowering stage or bolting stage. Bolting is the growth of an elongated stalk with flowers grown from within the main stem of a plant. During the bolting stage it is not possible anymore to harvest any marketable product of the plant.

The leaves of a spinach plant are usually sold loose, bunched, in prepackaged bags, canned, or frozen. There are three basic types of spinach, namely savoy, semi-savoy and smooth. Savoy has dark green, crinkly and curly leaves. Flat or smooth leaf spinach has broad smooth leaves. Semi-savoy is a hybrid variety with slightly crinkled leaves.

Downy mildew is probably the most widespread and potentially destructive global disease of spinach. The causal agent of downy mildew disease on various plants of Chenopodiaceae, including spinach, is regarded as a single species, *Peronospora farinosa*. Some of the forms on important crop plants have been given names as *formae speciales*, so f. sp. *spinaciae* on spinach. Downy mildew affects the harvested part (leaves) of spinach (*Spinacia oleracea*). Yellow lesions appear on the older leaves. Although some fungicide treatments are effective, they are costly and cause ecological pollution. There is a need for resistant spinach cultivars. There are currently 13 recognised described *P. farinosa* races (races pf1 to pf13) of *Peronospora farinosa* f. sp. *spinaciae* and a number of isolates not officially recognized yet. Although the pathogen was first reported early in the eighteenth century, only three races of the pathogen had been identified before 1990. More than ten new races of the pathogen were identified between 1990 and 2010, and some of the newer races had overcome all known genetic resistance. The rapid ascendance of new races is likely to be a result of intensification and scaling-up in spinach production during the past decade.

Citation or identification of any document in this application is not an admission that such document is available as prior art to the present invention.

SUMMARY OF THE INVENTION

The present invention provides a spinach plant showing a new resistance pattern against downy mildew (*Peronospora farinosa* f. sp. *spinaciae*) strains Pf1-Pf13. Seeds of a new spinach plant showing a new resistance pattern against downy mildew (*Peronospora farinosa* f. sp. *spinaciae*) strains Pf1-Pf13 have been deposited with the National Collections of Industrial, Marine and Food Bacteria (NCIMB) in Bucksburn, Aberdeen AB21 9YA, Scotland, UK and have been assigned NCIMB Accession No. 41820.

In one embodiment, the invention provides a spinach plant expressing a new resistance pattern against downy mildew (*Peronospora farinosa* f. sp. *spinaciae*) strains Pf1-Pf13.

In one embodiment, the invention provides a spinach plant exhibiting a combination of traits including resistance against downy mildew (*Peronospora farinosa* f. sp. *spinaciae*) strains Pf1-Pf13, and first foliage leaves with an elliptic shape, representative seed of which have been deposited under NCIMB accession No. 41820.

In one embodiment, the invention provides a spinach plant exhibiting a combination of traits including resistance against downy mildew (*Peronospora farinosa* f. sp. *spinaciae*) strains Pf1-Pf13, first foliage leaves with an elliptic shape and first foliage leaves with a pointed tip, representative seed of which have been deposited under NCIMB accession No. 41820.

In one embodiment, the invention provides a spinach plant designated 51-326, representative seed of which have been deposited under NCIMB Accession No. 41820.

In one embodiment, the invention provides a spinach plant with all the morphological and physiological characteristics of a hybrid spinach variety 51-326, representative seed of which have been deposited under NCIMB Accession No. 41820.

In one embodiment there is a plant grown from seeds, representative seed of which have been deposited under NCIMB Accession No. 41820.

In one embodiment the present invention relates to parts of a spinach plant of the invention, a spinach plant expressing a new resistance pattern against downy mildew (*Peronospora farinosa* f. sp. *spinaciae*) strains Pf1-Pf13, wherein the plant parts are involved in sexual reproduction, which include, without limitation, microspores, pollen, ovaries, ovules, embryo sacs or egg cells.

In addition, the invention relates to parts of the plant that are suitable for vegetative reproduction, which include, without limitation, cuttings, roots, stems, cells, and protoplasts of the spinach plants of the invention.

In one embodiment the invention relates to a tissue culture of regenerable cells of the plant of the invention. Such a tissue culture may be derived, without limitation, from leaves, microspores, pollen, ovaries, ovules, embryo sacs or egg cells, cotyledon, hypocotyls, meristematic cells, roots, root tips, anthers, flowers, seeds and stems. The plants of the invention from which such parts may come from, include those of which representative seed having been deposited under NCIMB Accession No. 41820.

In one embodiment, there is provided progeny of a spinach plant expressing a new resistance pattern against downy mildew (*Peronospora farinosa* f. sp. *spinaciae*) strains Pf1-Pf13, produced by sexual or vegetative reproduction, grown from seeds, regenerated from the above-described plant parts, or regenerated from the above-described tissue culture of the hybrid spinach variety or a progeny plant thereof, representative seed of which having been deposited under NCIMB Accession No. 41820.

As used herein, a plant of the invention and/or a spinach plant of the invention may encompass a spinach plant having, expressing and showing a new resistance pattern against downy mildew (*Peronospora farinosa* f. sp. *spinaciae*) strains Pf1-Pf13, first foliage leaves with an elliptic shape and/or first foliage leaves with a pointed tip. A plant of the invention and/or a spinach plant of the invention may be designated 51-326 or have all the morphological, physiological and/or genetic characteristics of a hybrid spinach variety 51-326, representative seed of which having been deposited under NCIMB Accession No. 41820.

In another embodiment, there is provided progeny of a spinach plant expressing a new resistance pattern against downy mildew (*Peronospora farinosa* f. sp. *spinaciae*) strains Pf1-Pf13, produced by sexual or vegetative reproduction, grown from seeds, regenerated from the above-described plant parts, or regenerated from the above-described tissue culture of the spinach plant of the invention or a progeny plant thereof, in which the regenerated plant expresses a new resistance pattern against downy mildew (*Peronospora farinosa* f. sp. *spinaciae*) strains Pf1-Pf13 or expresses a new resistance pattern, representative seed of which having been deposited under NCIMB Accession No. 41820.

Progeny of a spinach plant expressing a new resistance pattern against downy mildew (*Peronospora farinosa* f. sp. *spinaciae*) strains Pf1-Pf13, representative seed of which have been deposited under NCIMB Accession No. 41820, may be modified in one or more other characteristics, in which the modification is a result of, for example and without limitation, mutagenesis or transformation with a transgene.

In one embodiment, there is provided progeny of a spinach plant expressing a new resistance pattern against downy mildew (*Peronospora farinosa* f. sp. *spinaciae*) strains Pf1-Pf13 produced by sexual or vegetative reproduction, grown from seeds, regenerated from the above-described plant parts, or regenerated from the above-described tissue culture of a spinach plant of the invention or a progeny plant thereof, in which the regenerated plant exhibits a combination of traits including resistance against downy mildew (*Peronospora farinosa* f. sp. *spinaciae*) strains Pf1-Pf13 as well as a relatively long narrow seedling cotyledon, and is modified in one or more other traits.

In another embodiment the invention relates to a method of producing an inbred spinach plant derived from a plant of the invention of which representative seed has been deposited under NCIMB Accession No. 41820, which may comprise of the steps: a) preparing a progeny plant derived from a spinach plant expressing a new resistance pattern against downy mildew (*Peronospora farinosa* f. sp. *spinaciae*) strains Pf1-Pf13 by crossing the plant of a spinach plant exhibiting a combination of traits including resistance against downy mildew (*Peronospora farinosa* f. sp. *spinaciae*) strains Pf1-Pf13, representative seed of which have been deposited under NCIMB Accession No. 41820 with a second spinach plant; b) crossing the progeny plant with itself or a second spinach plant to produce a seed of a progeny plant of a subsequent generation; c) growing a progeny plant of a subsequent generation from said seed and crossing the progeny plant of a subsequent generation with itself or a second spinach plant; and d) repeating step b) or c) for at least 1 more generation to produce an inbred spinach plant derived from a spinach plant expressing a new resistance pattern against downy mildew (*Peronospora farinosa* f. sp. *spinaciae*) strains Pf1-Pf13.

It is noted that in this disclosure and particularly in the claims, terms such as "comprises", "comprised", and "comprising" and the like (e.g., "includes", "included", "including", "contains", 'contained', "containing", "has", "had", "having", etc.) can have the meaning ascribed to them in US Patent law, i.e., they are open ended terms. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits. Similarly, the terms "consists essentially of" and "consisting essentially of" have the meaning ascribed to them in US Patent law, e.g., they allow for elements not explicitly recited, but exclude elements that are found in the prior art or that affect a basic or novel characteristic of the invention. See also MPEP §2111.03. In addition, the term "about" is used to indicate that a value includes the standard deviation of error for the device or method being employed to determine the value.

These and other embodiments are disclosed or are obvious from and encompassed by the following Detailed Description.

DEPOSIT

The Deposit with NCIMB Ltd, Ferguson Building, Craibstone Estate, Bucksburn, Aberdeen AB21 9YA, UK, under deposit accession number NCIMB 41820 was made on 17 Mar. 2011 and was pursuant to the terms of the Budapest Treaty. Upon issuance of a patent, all restrictions upon the deposit will be removed, and the deposit is intended to meet the requirements of 37 CFR §§1.801-1.809. The deposit will be irrevocably and without restriction or condition released to the public upon the issuance of a patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, including the examples, given by way of example, but not intended to limit the invention solely to the specific embodiments described, may be best understood in conjunction with the accompanying drawings, incorporated herein by reference, in which FIG. 1 shows the leaf, the leaf base and leaf tip shapes of first foliage leaves.

DETAILED DESCRIPTION OF THE INVENTION

The invention provides methods and compositions relating to plants, seeds and derivatives of spinach plants which may comprise a new characteristic, showing resistance to downy mildew (*Peronospora farinosa* f. sp. *spinaciae*) strains Pf1-Pf13. A spinach plant with this new characteristic will be herein referred to as hybrid spinach variety 51-326. Hybrid spinach variety 51-326 is a commercial spinach hybrid distinct from other such hybrids.

The parents of hybrid spinach variety 51-326 were developed as follows: The mother is an inbred spinach line made from pedigree selection from 06.99113. After 4 selection and selfing cycles, a final round of selection was performed, selecting for uniformity. The father line of 51-326 is an inbred spinach line selection from 05.89240, obtained by 4 selection and inbreeding cycles, and a final round of backcross and selfing followed by selection.

Crossing the described mother and father inbred spinach lines with one another will yield uniform F1 hybrid progeny plants. Table 1 shows the pedigree scheme of the mother line, table 2 shows the pedigree scheme of the father line of hybrid spinach line 51-326.

The F1 may be self-pollinated to produce a segregating F2 generation. Individual plants may then be selected which represent the desired phenotype in each generation (F3, F4, F5, etc.) until the traits are homozygous or fixed within a breeding population.

TABLE 1

Breeding history of Mother line of 51-326 (M = mass selection, S = Selfing).

| Year 1 | F1 Pedigree selection from 06.99113 |
| Year 2 | S1F1 Generation grown |
| Year 3 | S2F1 Generation grown |
| Year 4 | S3F1 Generation grown |

TABLE 2

Breeding history of Father line of 51-326 (M = mass selection, S = selfing, B = backcrossing).

| Year 1 | F1 Pedigree selection from 05.89240 |
| Year 2 | S1F1 Generation grown |
| Year 3 | S2F1 generation grown |
| Year 4 | S3F1 generation grown |
| Year 5 | B1S3F1 generation grown |

In one embodiment, a plant of the invention has all the morphological and physiological characteristics of hybrid spinach variety 51-326.

The physiological and morphological differences with regards to the early plant development stages and bolting between hybrid spinach variety 51-326 and closest known variety "Racoon" are summarized in table 3.

Embodiments of the invention advantageously have one or more, and most advantageously all, of these characteristics.

TABLE 3

Physiological and morphological characteristics of hybrid spinach variety 51-326 in comparison with closest known variety "Racoon".

| | Cultivar | |
| --- | --- | --- |
| Line | 51-326 | Racoon |
| Species | *Spinacia oleracea* L. | *Spinacia oleracea* L. |
| Ploidy | Diploid | Diploid |
| Maturity, Growth rate | Medium to Fast | Fast |
| Seedling Cotyledon | | |
| Width (mm) | 7 | 7 |
| Length (mm) | 61 | 55 |
| Tip | Pointed | Pointed |
| Color Chart Value | 146A | 146A |
| Leaf (First Foliage Leaves) | | |
| Leaf Shape | Elliptic | Ovate |
| Leaf base | Straight | Straight |
| Leaf Tip | Pointed | Round-pointed |
| Leaf Margin | Flat | Flat |
| Color Chart Value Upper Surface Color | 137A | 146A |

TABLE 3-continued

Physiological and morphological characteristics of hybrid spinach variety 51-326 in comparison with closest known variety "Racoon".

| | Cultivar | |
| --- | --- | --- |
| Line | 51-326 | Racoon |
| Lower surface Color Color chart value | 146A | 146B |

In an embodiment, the invention relates to spinach plants that have all the morphological and physiological characteristics of the invention and have acquired said characteristics by introduction of the genetic information that is responsible for the characteristics from a suitable source, either by conventional breeding, or genetic modification, in particular by cisgenesis or transgenesis.

Cisgenesis is genetic modification of plants with a natural gene, coding for an (agricultural) trait, from the crop plant itself or from a sexually compatible donor plant.

Transgenesis is genetic modification of a plant with a gene from a non-crossable species or a synthetic gene.

Just as useful traits that may be introduced by backcrossing, useful traits may be introduced directly into the plant of the invention, by genetic transformation techniques; and, such plants of the invention that have additional genetic information introduced into the genome or that express additional traits by having the DNA coding there for introduced into the genome via transformation techniques, are within the ambit of the invention, as well as uses of such plants, and the making of such plants.

Genetic transformation may therefore be used to insert a selected transgene into the plant of the invention, or may, alternatively, be used for the preparation of transgenes which may be introduced by backcrossing. Methods for the transformation of plants, including spinach, are well known to those of skill in the art.

Vectors used for the transformation of spinach cells are not limited so long as the vector may express an inserted DNA in the cells. For example, vectors which may comprise promoters for constitutive gene expression in spinach cells (e.g., cauliflower mosaic virus 35S promoter) and promoters inducible by exogenous stimuli may be used. Examples of suitable vectors include pBI binary vector. The "spinach cell" into which the vector is to be introduced includes various forms of spinach cells, such as cultured cell suspensions, protoplasts, leaf sections, and callus. A vector may be introduced into spinach cells by known methods, such as the polyethylene glycol method, polycation method, electroporation, *Agrobacterium*-mediated transfer, particle bombardment and direct DNA uptake by protoplasts. To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. An illustrative embodiment of a method for delivering DNA into plant cells by acceleration is the Biolistics Particle Delivery System, which may be used to propel particles coated with DNA or cells through a screen, such as a stainless steel or Nytex screen, onto a surface covered with target spinach cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species, including a plant of inbred spinach line 51-326.

*Agrobacterium*-mediated transfer is another widely applicable system for introducing gene loci into plant cells. An advantage of the technique is that DNA may be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations. Moreover, advances in vectors for *Agrobacterium*-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes. Additionally, *Agrobacterium* containing both armed and disarmed Ti genes may be used for transformation. In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells, including spinach plant cells, is well known in the art (See, e.g., U.S. Pat. Nos. 7,250,560 and 5,563,055).

Transformation of plant protoplasts also may be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for spinach plant gene expression include, but are not limited to, the cauliflower mosaic virus (CaMV) P-35S promoter, a tandemly duplicated version of the CaMV 35S promoter, the enhanced 35S promoter (P-e35S), the nopaline synthase promoter, the octopine synthase promoter, the figwort mosaic virus (P-FMV) promoter (see U.S. Pat. No. 5,378,619), an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, the promoter for the thylakoid membrane proteins from spinach (psaD, psaF, psaE, PC, FNR, atpC, atpD, cab, rbcS) (see U.S. Pat. No. 7,161,061), the CAB-1 promoter from spinach (see U.S. Pat. No. 7,663,027), the promoter from maize prolamin seed storage protein (see U.S. Pat. No. 7,119,255), and other plant DNA virus promoters known to express in plant cells. A variety of plant gene promoters that are regulated in response to environmental, hormonal, chemical, and/or developmental signals may be used for expression of an operably linked gene in plant cells, including promoters regulated by (1) heat, (2) light (e.g., pea rbcS-3A promoter, maize rbcS promoter, or chlorophyll a/b-binding protein promoter), (3) hormones, such as abscisic acid, (4) wounding (e.g., wun1, or (5) chemicals such as methyl jasmonate, salicylic acid, or Safener. It may also be advantageous to employ organ-specific promoters.

Exemplary nucleic acids which may be introduced to the spinach plant of this invention include, for example, DNA sequences or genes from another species, or even genes or sequences which originate with or are present in spinach species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA may include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant of the invention. Non-limiting examples of particular genes and corresponding phenotypes one may choose to introduce into a spinach plant include one or more genes for insect tolerance, pest tolerance such as genes for fungal disease control, herbicide tolerance, and genes for quality improvements such as yield, nutritional enhancements, environmental or stress tolerances, or any desirable changes in plant physiology, growth, development, morphology or plant product(s).

Alternatively, the DNA coding sequences may affect these phenotypes by encoding a non-translatable RNA molecule that causes the targeted inhibition of expression of an endogenous gene, for example via antisense- or cosuppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present invention. (See also U.S. Pat. No. 7,576,262, "Modified gene-silencing RNA and uses thereof."

U.S. Pat. Nos. 7,230,158, 7,122,720, 7,081,363, 6,734,341, 6,503,732, 6,392,121, 6,087,560, 5,981,181, 5,977,060, 5,608,146, 5,516,667, each of which, and all documents cited therein are hereby incorporated herein by reference, consistent with the above INCORPORATION BY REFERENCE section, are additionally cited as examples of U.S. patents that may concern transformed spinach and/or methods of transforming spinach or spinach plant cells, and techniques from these US patents, as well as promoters, vectors, etc., may be employed in the practice of this invention to introduce exogenous nucleic acid sequence(s) into a plant of hybrid spinach variety 51-326 (or cells thereof), and exemplify some exogenous nucleic acid sequence(s) which may be introduced into a plant of hybrid spinach variety 51-326 (or cells thereof) of the invention, as well as techniques, promoters, vectors etc., to thereby obtain further plants of hybrid spinach variety 51-326, plant parts and cells, seeds, other propagation material harvestable parts of these plants, etc. of the invention, e.g. tissue culture, including a cell or protoplast, such as an embryo, meristem, cotyledon, pollen, leaf, anther, root, root tip, pistil, flower, seed or stalk.

The invention further relates to propagation material for producing plants of the invention. Such propagation material may comprise inter alia seeds of the claimed plant and parts of the plant that are suitable for sexual reproduction. Such parts are for example selected from the group consisting of seeds, microspores, pollen, ovaries, ovules, embryo sacs and egg cells. In addition, the invention relates to propagation material which may comprise parts of the plant that are suitable for vegetative reproduction, for example cuttings, roots, stems, cells, protoplasts.

According to a further aspect thereof the propagation material of the invention may comprise a tissue culture of the claimed plant. The tissue culture may comprise regenerable cells. Such tissue culture may be derived from leaves, pollen, embryos, cotyledon, hypocotyls, meristematic cells, roots, root tips, anthers, flowers, seeds and stems. (See generally U.S. Pat. No. 7,041,876 on spinach being recognized as a plant that may be regenerated from cultured cells or tissue).

Also, the invention comprehends methods for producing a seed of a "51-326"-derived spinach plant which may comprise (a) crossing a plant of hybrid spinach variety 51-326, representative seed of which having been deposited under NCIMB Accession No. 41820, with a second spinach plant, and (b) whereby seed of a "51-326"-derived spinach plant form (e.g., by allowing the plant from the cross to grow to producing seed). Such a method may further comprise (c) crossing a plant grown from "51-326"-derived spinach seed with itself or with a second spinach plant to yield additional "51-326"-derived spinach seed, (d) growing the additional "51-326"-derived spinach seed of step (c) to yield additional "51-326"-derived spinach plants, and (e) repeating the crossing and growing of steps (c) and (d) to generate further "51-326"-derived spinach plants.

The invention further involves a method of determining the genotype of a plant of hybrid spinach variety 51-326, representative seed of which has been deposited under NCIMB Accession No. 41820, or a first generation progeny thereof, which may comprise obtaining a sample of nucleic acids from said plant and detecting in said nucleic acids a plurality of polymorphisms. This method may additionally comprise the step of storing the results of detecting the plurality of polymorphisms on a computer readable medium and/or transmitting the results of detecting the plurality of polymorphisms, e.g., by telephony or by means of computer (e.g., via email). The plurality of polymorphisms are indicative of and/or give rise to the expression of the morphological and physiological characteristics of hybrid spinach variety 51-326.

The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

As used herein "database" refers to any representation of retrievable collected data including computer files such as text files, database files, spreadsheet files and image files, printed tabulations and graphical representations and combinations of digital and image data collections. In a preferred aspect of the invention, "database" refers to a memory system that may store computer searchable information.

As used herein, "computer readable media" refers to any medium that may be read and accessed directly by a computer. Such media include, but are not limited to: magnetic storage media, such as floppy discs, hard disc, storage medium and magnetic tape; optical storage media such as CD-ROM; electrical storage media such as RAM, DRAM, SRAM, SDRAM, ROM; and PROMs (EPROM, EEPROM, Flash EPROM), and hybrids of these categories such as magnetic/optical storage media. A skilled artisan may readily appreciate how any of the presently known computer readable mediums may be used to create a manufacture which may comprise computer readable medium having recorded thereon a polymorphism of the present invention.

As used herein, "recorded" refers to the result of a process for storing information in a retrievable database or computer readable medium. For instance, a skilled artisan may readily adopt any of the presently known methods for recording information on computer readable medium to generate media which may comprise the polymorphisms of the present invention. A variety of data storage structures are available to a skilled artisan for creating a computer readable medium where the choice of the data storage structure will generally be based on the means chosen to access the stored information. In addition, a variety of data processor programs and formats may be used to store the polymorphisms of the present invention on computer readable medium.

The present invention further provides systems, particularly computer-based systems, which contain the polymorphisms described herein. Such systems are designed to identify the polymorphisms of this invention. As used herein, "a computer-based system" refers to the hardware, software and memory used to analyze the polymorphisms. A skilled artisan may readily appreciate that any one of the currently available computer-based system are suitable for use in the present invention.

Spinach leaves are sold in packaged form, including without limitation as pre-packaged spinach salad or as canned spinach or as frozen spinach. Mention is made of U.S. Pat. No. 5,523,136, incorporated herein by reference consistent with the above INCORPORATION BY REFERENCE section, which provides packaging film, and packages from such packaging film, including such packaging containing leafy produce, and methods for making and using such packaging film and packages, which are suitable for use with the spinach leaves of the invention. Thus, the invention comprehends the use of and methods for making and using the leaves of the spinach of the invention, as well as leaves of spinach derived from the invention. The invention further relates to a container which may comprise one or more plants of the invention, or one or more spinach plants derived from a plant of the invention, in a growth substrate for harvest of leaves from the plant in a domestic environment. This way the consumer may pick very fresh leaves for use in salads. More generally, the invention includes one or more plants of the invention or one or more plants derived from spinach of the invention, wherein the plant is in a ready-to-harvest condition, including with the consumer picking his own, and further including a container which may comprise one or more of these plants.

The invention is further described by the following numbered paragraphs:

1. A spinach plant resistant against downy mildew (*Peronospora farinosa* f. sp. *Spinaciae*) strains Pf1-Pf13, representative seed of which having been deposited under NCIMB Accession NCIMB 41820.
2. A spinach plant of paragraph 1 exhibiting a combination of traits including resistance against downy mildew (*Peronospora farinosa* f. sp. *Spinaciae*) strains Pf1-

Pf13, and first foliage leaves with an elliptic shape, representative seed of which having been deposited under NCIMB Accession NCIMB 41820.

3. A spinach plant of paragraph 1 exhibiting a combination of traits including resistance against downy mildew (*Peronospora farinosa* f. sp. *Spinaciae*) strains Pf1-Pf13, first foliage leaves with an elliptic shape and first foliage leaves with a pointed tip, representative seed of which having been deposited under NCIMB Accession NCIMB 41820.

4. A hybrid spinach variety designated 51-326, representative seed of which having deposited under NCIMB Accession NCIMB 41820.

5. A spinach plant having all the morphological and physiological characteristics of a plant of paragraph 4, representative seed of which having been deposited under NCIMB Accession NCIMB 41820.

6. Seed of the plant of paragraph 1 or paragraph 2 or paragraph 3 or paragraph 4 or paragraph 5.

7. Parts of the plant of paragraph 1 or paragraph 2 or paragraph 3 or paragraph 4 or paragraph 5, wherein said parts of the plant are suitable for sexual reproduction.

8. Parts of the plant of paragraph 7, said parts selected from the group consisting of microspores, pollen, ovaries, ovules, embryo sacs and egg cells.

9. Parts of the plant of paragraph 1 or paragraph 2 or paragraph 3 or paragraph 4 or paragraph 5, wherein said parts of the plant are suitable for vegetative reproduction.

10. Parts of the plant of paragraph 9, said parts selected from the group consisting of cuttings, roots, stems, cells and protoplasts.

11. A tissue culture of regenerable cells from the spinach plant of paragraph 1 or paragraph 2 or paragraph 3 or paragraph 4 or paragraph 5.

12. A tissue culture of paragraph 11, wherein said cells or protoplasts of the tissue culture which are derived from a tissue selected from the group consisting of leaves, pollen, embryos, cotyledon, hypocotyls, meristematic cells, roots, root tips, anthers, flowers, seeds and stems.

13. Progeny of a spinach plant of paragraph 1 or paragraph 2 or paragraph 3 or paragraph 4 or paragraph 5.

14. Progeny of paragraph 13, wherein said progeny is produced by sexual or vegetative reproduction of said spinach plant.

15. Progeny of a spinach plant of paragraph 1 or paragraph 2 or paragraph 3 or paragraph 4 or paragraph 5, wherein the plant exhibits a combination of traits including resistance to downy mildew (*Peronospora farinosa* f. sp. *Spinaciae*) strains Pf1-Pf13, representative seed of which having been deposited under NCIMB Accession NCIMB 41820, and is modified in one or more other characteristics.

16. Progeny of paragraph 15, wherein the modification is effected by mutagenesis.

17. Progeny of paragraph 15, wherein the modification is effected by transformation with a transgene.

18. A method of producing an inbred spinach plant derived from hybrid spinach variety 51-326, comprising the steps:
    a) preparing a progeny plant derived from hybrid spinach variety 51-326 by crossing the plant of paragraph 1 with a second spinach plant;
    b) crossing the progeny plant with itself or a second spinach plant to produce a seed of a progeny plant of a subsequent generation;
    c) growing a progeny plant of a subsequent generation from said seed and crossing the progeny plant of a subsequent generation with itself or a second spinach plant;
    d) d) repeating step b) or c) for at least 1 more generation to produce an inbred spinach plant derived from the hybrid spinach variety 51-326.

19. A inbred spinach plant produced by the method of paragraph 18.

20. A method for producing spinach leaves as a fresh vegetable comprising packaging leaves of a plant of paragraph 1 or paragraph 2 or paragraph 3 or paragraph 4 or paragraph 5.

21. A method for producing spinach leaves as a processed food comprising processing leaves of a plant of paragraph 1 or paragraph 2 or paragraph 3 or paragraph 4 or paragraph 5.

22. One or more spinach plants of paragraph 1 or paragraph 2 or paragraph 3 or paragraph 4 or paragraph 5, in a container, for harvest of leaves.

23. A method of determining the genotype of a plant of hybrid spinach variety 51-326, representative seed of which has been deposited under NCIMB Accession NCIMB 41820, or a first generation progeny thereof, comprising obtaining a sample of nucleic acids from said plant and detecting in said nucleic acids a plurality of polymorphisms, wherein the plurality of polymorphisms are indicative of and/or give rise to the expression of the morphological and physiological characteristics of inbred hybrid spinach variety 51-326.

24. The method of paragraph 23 additionally comprising the step of storing the results of detecting the plurality of polymorphisms on a computer readable medium, or transmitting the results of detecting the plurality of polymorphisms.

25. The computer readable medium of paragraph 24.

Having thus described in detail preferred embodiments of the present invention, it is to be understood that the invention is not to be limited to particular details set forth in the above description as many apparent variations thereof are possible without departing from the spirit or scope of the present invention.

What is claimed is:

1. A plant of a hybrid spinach variety designated 51-326, resistant against downy mildew (*Peronospora farinosa* f. sp. *spinaciae*) strains Pf1-Pf13, representative seed of which having been deposited under NCIMB Accession No. 41820.

2. A spinach plant having all the morphological and physiological characteristics of a plant as claimed in claim 1, representative seed of which having been deposited under NCIMB Accession No. 41820.

3. A part of the plant of claim 1, wherein said part of the plant is suitable for vegetative reproduction and is a cutting, a root, a stem, a cell or a protoplast.

4. A tissue culture of regenerable cells or protoplasts from the spinach plant of claim 1, wherein the cells or protoplasts of the tissue culture are derived from a leaf, an embryo, a cotyledon, a hypocotyl, a meristematic cell, a root, a root tip, an anther, a flower, or a stem.

5. A spinach plant produced by transforming the spinach plant of claim 1 with a transgene.

6. A method of producing a spinach plant derived from hybrid spinach variety 51-326, representative seed of which having been deposited under NCIMB Accession No. 41820, comprising the steps: a) preparing a progeny plant derived from hybrid spinach variety 51-326 by crossing the plant of claim 4 with a second spinach plant; b) crossing the progeny plant with itself or a second spinach plant to produce a seed of a progeny plant of a subsequent generation; c) growing a progeny plant of a subsequent generation from said seed and crossing the progeny plant of a subsequent generation with itself or a second spinach plant; d) repeating step b) and c) for at least 1 more generation to produce an inbred spinach plant derived from the hybrid spinach variety 51-326.

7. A method for producing spinach leaves as a fresh vegetable comprising packaging leaves of a plant of claim 1.

8. A method for producing spinach leaves as a processed food comprising processing leaves of a plant of claim 1.

9. A container comprising one or more spinach plants of claim 1, for harvest of leaves.

10. A method of determining the genotype of a plant of hybrid spinach variety 51-326, representative seed of which has been deposited under NCIMB Accession No. 41820, comprising obtaining a sample of nucleic acids from said plant and detecting in said nucleic acids a plurality of polymorphisms, wherein the plurality of polymorphisms are indicative of and/or give rise to the expression of the morphological and physiological characteristics of hybrid spinach variety 51-326.

11. The method of claim 10 additionally comprising the step of storing the results of detecting the plurality of polymorphisms on a computer readable medium, or transmitting the results of detecting the plurality of polymorphisms.

12. The plant of claim 1, which is a plant grown from seed having been deposited under NCIMB Accession No. 41820.

13. A spinach plant having all the morphological and physiological characteristics of the hybrid spinach variety of claim 1, representative seed of which having been deposited under NCIMB Accession No. 41820.

14. A seed of the plant of claim 1, wherein the seed is capable of growing into a plant resistant against downy mildew (*Peronospora farinosa* f. sp. *spinaciae*) strains Pf1-Pf13, representative seed of which having been deposited under NCIMB Accession No. 41820.

* * * * *